United States Patent [19]

Cinquin et al.

[11] Patent Number: 5,447,154
[45] Date of Patent: Sep. 5, 1995

[54] METHOD FOR DETERMINING THE POSITION OF AN ORGAN

[75] Inventors: Philippe Cinquin; Stephane Lavallee, both of Grenoble; Francis Dubois, Meylan; Lionel Brunie, Grenoble; Jocelyne Troccaz, Eybens; Olivier Peria, Aix-les-Bains; Bruno Mazier, Grenoble, all of France

[73] Assignee: Universite Joseph Fourier, Grenoble, France

[21] Appl. No.: 99,334

[22] Filed: Jul. 30, 1993

[30] Foreign Application Priority Data

Jul. 31, 1992 [FR] France .................. 92 09801
Nov. 27, 1992 [FR] France .................. 92 14594

[51] Int. Cl.⁶ .................................................. A61B 5/05
[52] U.S. Cl. ........................... 128/653.1; 128/660.01
[58] Field of Search ........... 128/653.1, 660.01, 660.04, 128/660.03; 601/2, 4; 364/413.13, 413.24, 413.25

[56] References Cited

U.S. PATENT DOCUMENTS

| | | |
|---|---|---|
| 4,618,978 | 10/1986 | Cosman . |
| 4,791,934 | 12/1988 | Brunnett ...................... 128/653.1 |
| 4,907,252 | 3/1990 | Aichinger et al. ............ 128/653.1 X |
| 5,060,650 | 10/1991 | Wurster et al. ............... 128/660.03 |
| 5,099,846 | 3/1992 | Hardy ........................... 128/653.1 |
| 5,151,856 | 9/1992 | Halmann et al. ........... 364/413.13 X |
| 5,197,476 | 3/1993 | Nowacki et al. .................. 601/4 X |
| 5,230,329 | 7/1993 | Duppo ................................... 601/4 |
| 5,257,998 | 11/1993 | Ota et al. ..................... 128/653.1 X |
| 5,261,404 | 11/1993 | Mick et al. ...................... 128/653.1 |
| 5,273,039 | 12/1993 | Fujiwara et al. ................ 128/653.1 |
| 5,291,889 | 3/1994 | Kenet et al. .................... 128/653.1 |
| 5,299,254 | 3/1994 | Dancer et al. .............. 128/653.1 X |

FOREIGN PATENT DOCUMENTS

| | | |
|---|---|---|
| 427358A1 | 5/1991 | European Pat. Off. . |
| 3908648A1 | 9/1990 | Germany . |
| 4021102A1 | 1/1991 | Germany . |
| WO92/04862 | 4/1992 | WIPO . |

OTHER PUBLICATIONS

S. Lavallée et al., "Matching 3D Smooth Surfaces With Their 2D Projections Using 3D Distance Maps", SPIE 1570, pp. 322–336, 1991.
F. Leitner et al., Dynamic Segmentation, "Finding The Edges With Spline Snakes", Proc. Int. Conf. on Curves and Surfaces, Chamonix, Academic Press, pp. 279–284, 1991.
Y. C. Shiu et al., "Finding The Mounting Position By Solving A Homogeneous Transform Equation Of Form AX–XB", IEEE, CH2413-3/87/0000/1666, 1987.
K. S. Arun et al. "Transactions on Pattern Analysis and Machine Intelligence", IEEE, vol. PAMI, 9, No. 5, pp. 698–700.

*Primary Examiner*—Lee S. Cohen
*Assistant Examiner*—Brian L. Casler
*Attorney, Agent, or Firm*—Lowe, Price, LeBlanc & Becker

[57] ABSTRACT

A method for determining the position of a patient's organ with respect to at least two imaging devices includes a step of making at least one three-dimensional first image of an organ of a patient giving a first coordinate system and of a surface of the organ or skin region using a first imaging device without fixing any mark to the patient, placing the patient in an operation site having a second coordinate system and determining a first position of a second imaging device with respect to the second coordinate system of the operation site. In addition, the method includes the steps of making a second image with the second imaging device, matching the first and second images and providing a third device having a third coordinate system. The third device is positioned with respect to the second image of the second device which thereby positions the third device with respect to the first image of the first imaging device.

10 Claims, 1 Drawing Sheet

METHOD FOR DETERMINING THE POSITION OF AN ORGAN

BACKGROUND OF THE INVENTION

The present invention relates to the field of surgery and of medical observation, and more particularly relates to methods and devices for positioning a therapeutic or diagnostic tool as a function of three-dimensional images, that can be images carried out before hand (preoperation images) of a patient's organ.

In the present application, "tool" is to be construed as any therapeutic or diagnostic means carried out on a patient. The tool can be, for example, a device adequate to insert a screw in a patient's bone, a needle to carry out a puncture or simply to guide an optical fiber, a radiation transmission apparatus designed to act on a tumor, or a medical imaging device such as a gamma-scintigraphy camera, a positron emission tomography (PET) apparatus, or a magnetoencephalography (MEG) apparatus.

In other words, an object of the invention is to recover, during a surgical procedure, the morphological information that previous three-dimensional (3D) examinations have provided. This situation is very frequently encountered in the medical domain. Two examples of such a situation are given below.

1. Radiotherapy

Radiotherapy consists in projecting onto a predetermined patient's region, or on one of his organs, a radiation beam so as to destroy or eliminate tumors existing in these organs. Such therapy treatments must generally be carried out periodically and repeatedly. Therefore, at each medical intervention, the radiation source must be repositioned with respect to the patient in order to irradiate the selected region with the highest possible accuracy to avoid irradiating adjacent patient's organs on which radiation beams would be harmful.

The initial diagnostic procedure has generally been carried out by an X-ray scanner or by magnetic resonance imaging (MRI) that allow to visualize the target site and the obstacles, and therefore to define an optimal therapeutic procedure. The difficulty is to reposition the patient when he must receive the therapy treatment. The method that is presently used consists in simulating the intervention by replacing the linear accelerator (radiation source) by an X-ray tube. Two radiographies (face and profile) of the patient are then obtained and are visually compared with the previous 3D information provided by the X-ray scanner or the MRI apparatus. The patient is moved, and radiographies are made again until the patient's positioning is deemed satisfactory. A light beam then materializes a marking on the patient's skin, and this marking is inscribed on the patient's skin itself with a marker. During the irradiation session, the patient is moved until these marks on this skin are in coincidence with light beams, that are identical for the linear accelerator and for the simulation radiologic system. This conventional method has numerous drawbacks. One of them is to necessitate moving the patient on the medical table so that he takes the desired position, which is not easy and may compel the patient to stay in an uncomfortable position, or cause the patient to be so crisped that he will not be able to stay in the desired position. It should be pointed out that the patient's position must be as accurate as possible. For example, in the case of the final radiotherapy session of the prostate, where this organ only, included within a sphere of 4 cm in diameter, is targeted, with the conventional methods, it is necessary to irradiate an area of 10 cm in diameter to ensure that the prostate is appropriately reached. Of course, this is not harmless for the adjacent organs.

2. Orthopedics

In orthopedics applications, the point is to provide an assistance for introducing an object (for example a screw) in the human body (usually into a bone) according to a linear path. The shape of the bone is conventionally studied by 3D imaging (X-ray scanner or MRI) and the procedure of the medical intervention is then defined as a function of this image, especially as regards the exact direction along which the tool must be inserted in order to reach exactly the desired position without passing through regions of the body where it can be harmful.

Conventionally, during the surgical procedure, radiography is used to control the introduction of the tool. Under usual conditions, the major drawback is that it is not possible to simultaneously make face and profile images both of the target and of the object to be introduced. This method can therefore be used only a posteriori, as a means for verifying the appropriate positioning of the object (the progression being tracked in real time on one projection only). Additionally, such a verification cannot be made quantitatively. The interpretation is made by the operator alone. Present studies show that with such techniques, in approximately 10% of cases, positioning is not ideal.

More recently, it has been proposed to improve the use of a radiologic system in an operation site to implement techniques for matching three-dimensional (3D) with two-dimensional (2D) images (refer to S. Lavallée et al., "Matching 3D smooth surfaces with their 2D projections using 3D Distance Maps" SPIE 1570, pp. 322-336, 1991). The problem with this method is that the technique is expensive because it requires the use of a sophisticated radiologic system capable of studying the target on several incidences and providing a signal that can be digitized. To avoid the drawbacks of the radiologic systems, some medical teams have proposed to make therapy interventions using X-ray scanner or MRI apparatus. It is then easy to make comparison between the pre-operation and on-site images that are carried out with the same means. However, such approaches have many drawbacks due to the fact that they involve the simultaneous use of sophisticated imaging tools and surgical tools. Among these drawbacks, can be cited:

surgical constraints (asepsis . . . ), long immobilization (for the duration of a surgical procedure) of expensive materials (X-ray scanner or MRI apparatus) while it is desirable to use such apparatuses continuously for observation tasks, for a better economy of operation, the need for specific surgical tools (in the case of the MRI system, these tools must not generate artifacts and, more particularly, must be non-ferromagnetic); this involves, for example, the use of very expensive tools made of titanium, the geometry of the imaging apparatuses (small-diameter channel) renders the introduction of the surgical tools difficult.

However, the development of such 3D image matching techniques, despite all the above-mentioned drawbacks, shows the interest of the medical teams in any means capable of improving the accuracy of the introduction of surgical tools.

SUMMARY OF THE INVENTION

An object of the invention is to provide a simple and inexpensive method for making a series of on-site images of an organ that allows to position a tool in a predetermined manner with respect to a series of 3D pre-operation images.

To achieve this object, the present invention provides the use, for making on-site images, of a device providing a 3D morphologic image of surface points of the organ of interest or a skin region fixed with respect to the organ. Then, this surface point image is combined (matched) with the pre-operation 3D functional image that also contains information on the localization of the surface points (of the organ or skin region).

To obtain a 3D morphologic image of the surface points of the organ, the invention provides the use of echography probes.

To obtain a 3D morphologic image of the surface points of a skin region fixed with respect to the organ (for example an image of a portion of the patient's head that is fixed with respect to the brain), the invention provides the use of optical imaging devices.

Further, the invention provides to align the coordinates of the tool with respect to the coordinate system of the organ which is in turn defined by the preoperation image.

A second object of the invention is the matching of an image from a second device that provides, as indicated, a 3D morphologic image of surface points associated with an organ, and an image from a specific apparatus disposed within the same surgical site, such as a gamma-scintigraphy camera, a positron emission tomography (PET) apparatus, a magnetoencephalography (MEG) apparatus, or a synchrotron radiation apparatus, that provides functional information on specific regions of this organ, thus making it possible to position these specific regions of the organ.

To achieve this second object, the invention provides for previously localizing an initial position of the first device and of the specific apparatus by making them pinpoint a same target that is visible by both of them (for example in ultra-sonic frequencies and in gamma rays in the case of an echography probe and of a gamma-scintigraphy camera).

One of the originalities of the invention lies in the use of a device that does not provide functional information but only images of surface points to serve as an intermediate device operable for matching different coordinate systems. In particular, the idea of using an echography probe to carry out this coordinate alignment is one of the aspects of the invention since, a priori, an echography image provides less valuable information than a MRI or scanner-type apparatus. Indeed, echography usually provides a series of plane and independent cross-sectional images of an organ instead of a volume image structured in series of parallel image slices.

Reminders on Echography

Echography is an imaging process that has been progressing since 1970. A transducer (piezoelectric crystal) emits ultra-sonic frequencies of several megahertz that spread in the human body, but can be reflected when they reach interfaces where the acoustic impedance of the medium presents high variations (typically, a water/grease interface). The same transducer can be used for a short period of time as an ultra-sonic frequency emitter, and, for a generally longer period of time, as a receiver for the ultrasonic frequencies reflected by the human body. It is then possible to measure both the time interval between the emission and reception (which allows, taking into account hypotheses on the speed of ultra-sonic frequencies in the considered medium, the localization of the echography source) and the echo intensity (which provides information on the nature of the echographing point).

The simplest operation modality is to emit and recover ultra-sonic frequencies in one direction only (mode A). Then, one obtains a signal that is variable as a function of time if the body's tissues targeted by echography are mobile. This operation mode was the first one to be used in medicine, particularly in cardiovascular applications (where it made it possible to assess the mobility of the hearth valves, for example).

It is also possible to emit and collect the ultrasonic frequencies in a plane portion of the space (mode B). This can be achieved by juxtaposing on a lineal rod a series of fixed mono-dimensional transducers, or by rotating (mechanically or electronically), within a plane, about a fixed point, a mono-dimensional transducer, Such an imaging modality has proven very valuable for the study of "soft organs", more particularly in gynecology, obstetrics and gastroenterology field.

Additionally, there exist many clinical situations in which echography provides the most valuable information (more particularly in the gastroenterology, gynecology-obstetrics and cardiology domains). Echographies are also very useful for guiding surgical procedures (they permit, for example, to control the introduction of puncture needles through the human body).

Additionally, the echography system has over an X-ray scanner and MRI apparatus the following advantages:

its cost is approximately 10 times lower,
the emitter can be fabricated in the form of a probe that is pressed on the body, and has a light and easily transportable structure; on the contrary, the X-ray scanner and MRI apparatuses are very cumbersome and occupy a large volume in an examination room,
as compared to the X-ray scanner, echography, like MRI, is absolutely harmless.

Above all, the main advantage of an echographic system to provide morphologic images lies in its simplicity of use and low cost.

Additionally, usual preconceptions disregard the echography system for orthopedics analyses, that is, for analyses of bones. Indeed, under common conditions, ultra-sonic frequencies do not pass through the bones that specularly reflect them. Therefore, it is impossible to study the inner portion of bones by using ultrasonic frequencies. The study of a bone surface is however possible, although it is rendered difficult because of the specular character of the reflection of ultra-sonic frequencies. Since the reflection is made practically only along the direction given by the Cartesian law, each echography of a bone gives images including little valuable information: only are seen portions of the outline of the bone whose normal is parallel to the direction of the ultra-sonic frequencies.

However, for the application that is envisaged here, it is sufficient, as will be described hereinafter, to collect a piece of information on a point of the surface of a bone at each echography session to implement the method according to the invention. Echography therefore also applies to orthopedics applications.

More particularly, the invention provides a method for determining the position of a patient's organ with respect to at least two imaging devices. The second imaging device is a device providing an image of points of the surface of an organ or of a skin region of the patient. This method includes the steps consisting in determining the position of the second device with respect to the coordinate system of the patient's support; making at least one cliché with the first device, whereby a second image corresponding to a cloud of points of the surface of the organ or of the skin region is obtained; making at least one 3D image of the organ and of its surface or of the surface of the skin region with the first imaging device; and matching the second image with the first image.

According to an embodiment of the invention, the second imaging device is an echography probe, capable of providing, at each view, the distances within a viewing plane between the probe and the interface between the organ and the adjacent medium. The imaging technique consists in moving the probe and making a cliché for each of the plurality of predetermined positions of the probe so as to obtain, for each cliché, the position with respect to the probe of at least one point of the surface of the organ, whereby a first image corresponding to a cloud of points of the organ surface is obtained.

According to an embodiment of the invention, the step of determining the position of the probe with respect to the coordinate system of the patient's support includes the steps consisting in fixing the probe onto an articulated arm of a coded robot, viewing three points of an echography sighting mark, rotating the probe by 180° about its viewing axis and viewing again the three points of the sighting mark, and resuming the two preceding steps for another position of the sighting mark.

According to an embodiment of the invention, the sighting mark is formed by three parallel threads tightened between two planes, and by three additional threads that are made of a material reflecting ultrasonic frequencies, and arranged in a triangle abutting against the three parallel threads. The set of threads is immersed in a medium capable of transmitting ultrasonic frequencies, such as a water vessel.

The invention provides a method for determining the position of the patient's organ in the on-site coordinate system in order to automatically position a tool disposed within this coordinate system according to a strategy, i.e. an orientation and a direction, that is defined by the results of the analysis of the organ made in a pre-operation coordinate system.

In this case, the second device is disposed on site, in an operation site associated with a first coordinate system, the first imaging device is disposed in a preoperation site associated with a second coordinate system, and the first imaging device is of a type adapted to provide a 3D image of the surface of the organ, and, if required, also of the skin surface, whereby the image matching step localizes the first coordinate system with respect to the second one.

A embodiment of the invention provides the steps consisting in determining an action axis of a surgical tool with relation to the pre-operation image taken in the first coordinate system, identifying this action axis in the first coordinate system, and positioning a tool according to this action axis in the second coordinate system. When the "surgical" tool is an analysis system mounted on a support placed in the operation site but independent of the support of the first device, the identification of the tool's action axis is made by viewing a same sighting mark by the second device and by the tool. When the second device is an echography probe and the tool is a radiotherapy apparatus having its sphere of action materialized by laser beams, the sighting mark that is common to the echography probe and to this tool is an echography sighting mark to which is added a cubic reflector positioned in a determined manner with respect to the latter.

The invention also provides to use this method to position a morphologic image with respect to a functional image of an organ, the functional image being made, for example, by a gamma-scintigraphy camera or a PET apparatus.

In this case, the second device is positioned in an operation site, and a third imaging device is used, such as a gamma-scintigraphy camera or PET, MEG or synchrotron-radiation apparatus, placed in the same operation site. The relative positions of the second device and third devices are defined by viewing a same sighting mark by the second and third devices. The image matching is made from this initial determination of the relative positions of the first and third devices.

According to an embodiment of the invention, in which the second device is an echography probe, and the third device is a gamma-scintigraphy or MEG apparatus, the sighting mark is formed by hollow catheters filled with a radioactive product, the sighting mark including four tubes arranged in a noncollinear manner between two parallel plates.

The foregoing and other objects, features, aspects and advantages of the invention will become apparent from the following detailed description of the present invention when taken in conjunction with the accompanying drawings.

DETAILED DESCRIPTION

Figure 1:
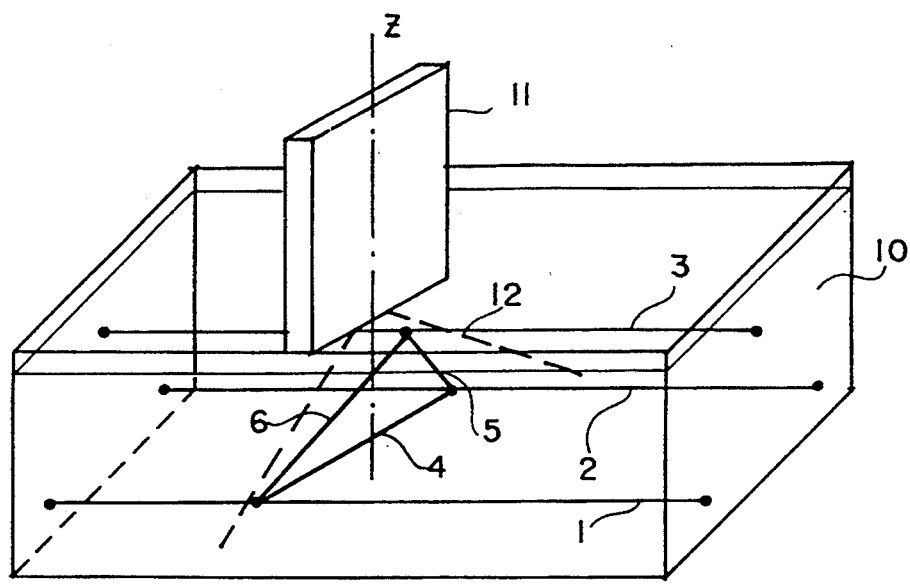
FIG. 1 illustrates an exemplary sighting mark used with an echography system according to the invention.

As reminded above, for several medical, diagnostic or therapeutic procedures, it is necessary to match (that is, to make correspond in a determined manner) a first coordinate system in which a previous, pre-operation, examination has permitted to study a portion of the anatomy and to determine a surgical procedure, and a second, on-site, coordinate system in which the surgical procedure is carried out. The prior art methods mainly consist in fixing fiducial marks visible both during the surgical procedure and during the pre-operation examination. As indicated above, such methods are often inaccurate and difficult to use.

The pre-operation examination must allow the identification of anatomic portions (a vertebra, a prostate, the brain . . . ) whose shape or the shape of the skin envelope (the skin of the skull for the brain) will serve as a reference for matching the coordinate systems. Thus, one considers the case where the coordinate systems are matched ("merged") as a function of the organ itself or of its skin envelope. Various image processing techniques can be used to implement these operations by using a so-called 3D segmentation step (refer to F. Leitner, I. Marque. S. Lavallée, P. Cinquin, Dynamic Segmentation: "Finding the Edges with Spline Snakes", Proc. Int. Conf. on Curves and Surfaces, Chamonix, Academic Press, pp. 279-284, (1991).

Using an echography probe

In an embodiment, the present invention aims at providing a method in which the on-site image results from a cloud of points obtained by echography examination of the region of interest, which permits visualizing objects that have been previously segmented.

The difficulty lies in the conception of a protocol that enables to associate the coordinates of the points that were observed in echography with the on-site coordinate system. To achieve this purpose, one must be capable of localizing the position of the echography probe in the on-site (surgical) coordinate system.

According to a first implementation of the invention, it is possible to provide on the probe itself landmarks detectable by an adequate sensor (for example, photoluminescent diodes, ultra-sonic frequency emitters) that is rigidly fixed with respect to the on-site coordinate system.

According to another preferred embodiment of the invention, the probe is rigidly fixed to the end of an articulated arm of a robot. Then, one determines both the position of the probe with respect to the articulated arm and the position of the coordinate system of the articulated arm with respect to the on-site coordinate system.

a) Determining the relative position of the probe with respect to the articulated arm To achieve this determination, the invention provides for determining the position of the probe with respect to a calibration sighting mark that permits to see in echography landmarks having a fixed spatial distribution. These landmarks are scanned by the echography device and their actual spatial position is compared with the position provided by the coordinate transformer of the robot's arm for a theoretical position of the probe. Then, by using a non-linear least square technique, it is possible to identify rotation and translation parameters that characterize the transition from the coordinate system of the probe to the one of the arm.

Since the probe is rigidly fixed to the arm's end, the transformation that associates the coordinate system of the probe with the coordinate system of the articulated arm must be found. To achieve this purpose, three reference points of a sighting mark, that have to be studied in at least two arbitrary positions, are studied.

One embodiment of a sighting mark according to the invention is illustrated in FIG. 1. The sighting mark includes, in a medium capable of transmitting ultrasonic frequencies, for example a water vessel 10, three threads 1, 2 and 3 tightened between two planes. Three additional threads, 4, 5, and 6 connect each couple of the three threads 1, 2 and 3, and form a triangular pattern. The triangle can be fabricated by a thin thread made of a material sensitive to echography system, such as a Nylon thread. Then, by means of the articulated arm manipulator (not shown), a probe 11 is arranged so that its plane beam 12 is coplanar with the plane of the three threads 4, 5 and 6. When the probe is within the triangle's plane, this triangle is then perfectly visualized and its apex is deducted by calculating the intersection of its edges. From this position of probe 11, the probe is rotated by 180° about axis Z comprised within the plane of the echography image, thus allowing to identify the rotation parameters.

The calibration sighting mark is moved to another arbitrary position so as to resume the visualization of the points of the sighting mark according to two positions of the articulated arm supporting the echography probe, the two positions being rotated one with respect to the other by 180°. Then, all the necessary data are available to implement a conventional calibration method, such as described, for example, by Y. C. Shiu et al., "Finding the Mounting Position by Solving a Homogeneous Transform Equation of Form AX=XB", CH24133/87/0000/1666, 1987, IEEE.

b) Determining the position of the fiducial mark of the articulated arm and of the probe with respect to the coordinate system of a surgical tool.

The surgical tool, for example a guide for introducing a needle, may have been worked simultaneously with the articulated arm carrying the probe. In that case, there is no particular positioning problem.

However, if the surgical tool was designed independently of the articulated arm carrying the probe, their coordinate systems have to be localized one with respect to the other.

In a first example, the surgical tool is a gammascintigraphy camera or a tomography apparatus, and a sighting mark visible by the echography and gamma-scintigraphy systems is used to calibrate the respective coordinate systems.

Figure 2:
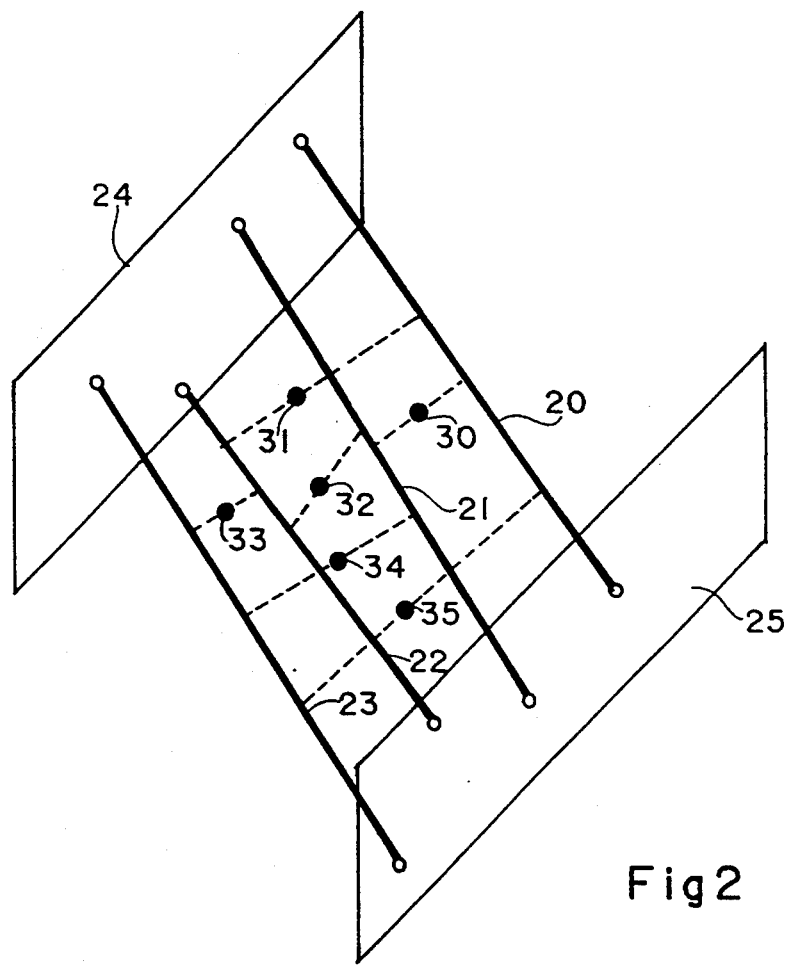
FIG. 2 schematically represents an exemplary dual echography/gamma-scintigraphy sighting mark used according to the invention.

FIG. 2 shows such an exemplary sighting mark comprised of four non-parallel threads (20-23) tightened between two parallel planes. The four threads are thin catheters stretched between two plates 24, 25 made of Plexiglass and are filled with a radioactive product. Once the sighting mark is placed in a water vessel, it can be seen both in echography and scintigraphy systems. On each cross-sectional scintigraphy view, four radioactive sources are detected, and on the echography probe, one directly observes the intersections of the four rods 20, 21, 22 and 23 that are stretched between the Plexiglass plates 24 and 25 with the echography plane. From these data, it is possible to restore the equations of the four lines 20, 21, 22, 23 in the coordinate system of the echography system and scintigraphy camera.

For each pair of rods 20, 21, 22, 23, one calculates a virtual point 30-35 defining the middle of the segment whose length is the minimum distance between two rods. One obtains a set of 6 points within the echography coordinate system and a set of 6 points within the camera coordinate system. It is then possible to apply a known minimizing method, for example the method described by K. S. Arun et al. in IEEE "Transactions on Pattern Analysis and Machine Intelligence", Vol. PAMI 9, No 5, pp 698-700.

In a second example, the surgical tool is a radiotherapy apparatus that is often associated with sources of laser beams allowing to localize an angle-shaped orthogonal-edged reflector. One uses as a sighting mark an echography sighting mark, for example as the one shown in FIG. 1, to which is fixed, in a well determined manner with respect to the three threads 4, 5, 6, a reflective edge that is positioned, for the initial calibration, at the intersection of the laser beams.

Once the echography probe is perfectly positioned with respect to the on-site (surgical) coordinate system, one applies the method according to the invention consisting in visualizing a cloud of image points of the surface of the organ of interest for several positions of the echography probe so as to determine the position of the probe with respect to the organ coordinate system that is defined by a 3D pre-operation image. It will then be possible to adapt the position of a tool localized with respect to the probe to a determined strategy determined during the pre-operation phase.

Additionally, once the echography probe is localized with respect to a dual sighting mark as the one of FIG. 2, one can pinpoint an initial position with respect to this dual sighting mark of an apparatus such as a gamma-scintigraphy or tomography camera. The echography probe is then moved in a determined manner with respect to this initial position, for example by an arm of a coded robot. Thus, one knows at any time the position of the camera with respect to the probe. It is therefore possible to match echographic (morphologic) images with gamma-scintigraphy or tomography (functional) images, which provides very useful information for the diagnostic procedure. Additionally, it is possible, as seen above, to match (merge) the echography images with a 3D morphologic image resulting from the analysis by an X-ray scanner or a MRI apparatus. The echographic images then serve as intermediate images, and the combination of these two types of image merging allows to match the gamma-scintigraphy image with the 3D morphologic image resulting from an X-ray scanner or a MRI analysis.

Of course, as is apparent to those skilled in the art, various modifications can be made to the above disclosed preferred embodiments, more particularly with respect to the selection of the echography images to be made, and the modes for providing a correlation between the pre-operation 3D images and the image of a cloud of points obtained by echography of a same organ.

Using an image of a skin region

As explained hereinabove, the organ to be localized can be fixed with respect to a skin region of the patient, as is the case of the brain with respect to the patient's head.

A variant of the invention proposes to use as "first device" a non-contact 3D surface imaging device. Preferably, such an imaging device is an optical device based on a global imaging or a scanning imaging.

a) Global methods

The Moiré's method is typical of global methods. One uses a structured light source, whose beam is partitioned into two sub-beams that are projected onto the object to be analyzed, and have two different optical paths, which result in interference fringes. The analysis of such interference fringes permits deducting information on the surface of the object.

b) Scanning methods

A laser scan is typical of scanning methods. In the simplest version, the surface is illuminated point-to-point with a laser beam, whose position is perfectly known. The scene is observed by a camera equipped with a filter corresponding to the wavelength of the laser, whose position with respect to the laser, as well as the characteristic parameters, had been previously determined by calibration. It is then easy to define, through a simple triangulation, the position of the intersection point between the laser and the object (which is actually the intersection of two lines of a known equation, the line of the laser, and the line connecting the observed point with the optical focus of the camera). A rotating mirror, that very rapidly moves the direction of the laser beam, is used to scan the object.

Such a method finds many applications in the industrial domain. The accuracy can be very high (it is possible to use extremely narrow laser beams, and-to take into account the gaussian feature of the beam, in order to obtain precisions of approximately a few tens of a $\mu$m, if required).

A variant of this method is to have the laser beam to pass through a cylindric lens, which provides a plane emergent beam. This plane beam is then projected onto the object, and its intersection with the object is analyzed by a camera disposed at a known position. In this case also, it is easy to deduct from the processing of the image thus obtained the spatial position of all the intersection points of the laser plane with the object. Then, it is merely necessary to translate the laser beam (or the object), or to rotate it about an axis, to "scan" the whole object, and to acquire the points of its surface.

Reminder on the Magnetoencephalography (MEG)

A function of a MEG apparatus is to study the activities of the brain, by analyzing its magnetic field emitted during the various cerebral activities. This magnetic field is very low (much lower than the earth magnetic field). The patient's head is placed into a device formed by several probes designed to collect the magnetic fields at the surface of the skull. The number of electrodes used is relatively limited (the most efficient apparatuses presently use 128 electrodes). In order to define a magnetic intensity map inside the brain, the conditions are much more unfavorable than, for example, the conditions for restoring tomodensitometric images from radiography projections. Indeed, on the one hand, the number of available data is much smaller (in tomodensitometry technique, for each cross-section view, several hundreds of projection measurement points, and several hundreds of projections are available) and, on the other hand, the propagation of the electromagnetic waves is highly variable depending on the electrophysiologic characteristics of the tissues that are traversed. The "reverse problem" to be solved for the MEG system is therefore much less accurately defined than for the tomodensitometry system. However, examinations that can be carried out prior to the MEG analysis provide information that is potentially of the greatest importance for the restoring of MEG images. The tomodensitometry system allows, for example, to perfectly identify the bones of the cranial cavity. The skull's bone is the most important obstacle for the diffusion of the electromagnetic waves emitted by the brain. The determination of its thickness and its precise localization are therefore very valuable information in MEG technique. The ventricle structures, whose electric characteristics are very specific, can also be perfectly identified. As for the MRI system, it permits to differentiate the grey substance from the white substance (that have different electric characteristics), and also to pinpoint potentially emitting regions. MEG examinations can indeed consist in recording the electric activity of the brain during well defined sensorimotor or imaginary tasks, that, as is known, activate very well known regions of the brain, that can be localized by the MRI system.

The above description is intended to stress the advantage of an easy and reliable method for repositioning the coordinate system of pre-operation examination systems, such as MRI or X-ray scanner, before beginning to calculate MEG images. Taking into account the "pre-MEG" information thus available provides substantially improved MEG images.

We claim:

1. A method for determining the position of a patient's organ with respect to at least two imaging devices, including the following steps:

making at least one 3D first image of an organ of a patient having a first coordinate system and of a surface of the organ or skin region with a first imaging device while the patient is in a pre-operation site without fixing any mark to the patient;

placing the patient in an operation site having a second coordinate system;

determining a first position of a second imaging device with respect to the second coordinate system of the operation site;

making a second image with said second imaging device, the second image corresponding to a cloud of points of the surface of the organ or skin region;

matching the at least one 3D first image and the second image where the at least one 3D first image is located with respect to the first coordinate system of the patient; and providing a third device having a third coordinate system in the operation site and determining a first position of the third device with respect to the second image of the second imaging device, whereby the third coordinate system of the third device is positioned with respect to the second image of the second imaging device and thereby with respect to the at least one 3D first image from the first imaging device.

2. The method of claim 1, wherein the second imaging device is an echography probe, capable of providing, at each actuation, distances within a viewing plane between said echography probe and an interface within said viewing plane between said organ and an adjacent medium, and wherein the method further comprises moving the echography probe and making a view for each of a plurality of predetermined positions of the echography probe so as to obtain, for each view, a position with respect to the echography probe of at least one point of the surface of the organ, whereby said second image corresponding to the cloud of points of the surface of the organ is obtained.

3. The method of claim 2, wherein the step of determining the position of the echography probe with respect to the second coordinate system of the operation site includes the steps of:

fixing the echographyprobe onto an articulated arm of a robot, pinpointing three points of an echography sighting mark, rotating the echography probe by 180° about a pinpoint axis and pinpointing again the three points of the echography sighting mark, and resuming the pinpointing and rotating steps for another position of the echography sighting mark.

4. The method of claim 3, wherein said pinpointing step further comprises the step of pinpointing three points of the echography sighting mark formed by three parallel threads (1–3) tightened between two planes, and by three additional threads (4–6) that are made of a material reflecting ultra-sonic frequencies, and wherein the three additional threads are arranged in a triangle abutting against the three parallel threads, the set of three parallel and additional threads being immersed in a medium capable of transmitting ultra-sonic frequencies.

5. A method for determining the position of a patient's organ according to claim 1, and for acting on said organ, wherein said third device is an operation tool, further comprising the following steps:

determining an action axis for said operation tool with respect to a pre-operation image taken in a first pre-operation coordinate system, identifying said action axis in the second coordinate system of the operation site, and positioning said operation tool according to said action axis in the second coordinate system of the operation site.

6. The method of claim 5, wherein the identifying step of the action axis of the operation tool, when said operation tool is an analysis system mounted on a support placed in the operation site but independent of the support of the second device, further comprises the step of pinpointing a same sighting mark in common with the second imaging device and said operation tool.

7. The method of claim 6, in which the second device is an echography probe and said operation tool is a radiotherapy apparatus having a sphere of act,ion materialized by laser beams, the step of pinpointing the same sighting mark common to the echography probe and to said operation tool further comprises the step of forming the same sighting mark according to the pinpointing three points step of claim 4 to which is added a cubic reflector having edges positioned in a determined manner with respect to said three additional threads, and wherein said cubic reflector is initially placed in said sphere of action by aligning the laser beams with the edges of the cubic reflector.

8. The method of claim 1, wherein:

said third device is an imaging device including one of a gamma-scintigraphy, PET, MEG or synchrotron radiation apparatus providing a third image, and the providing step further comprises the steps of:

defining relative positions of the second imaging device and the third device by viewing a sighting mark in the operation site with the second imaging device and the third device, and matching the at least one 3D image and the third image of she first imaging device and the third device.

9. The method of claim 8, wherein the second imaging device is an echography probe and the third device belongs to a group comprising a gamma-scintigraphy camera and a MEG apparatus, and said defining step further comprising the step of forming the sighting mark using hollow catheters filled with a radioactive product, the sighting mark including four tubes arranged in a non-collinear manner between two parallel plates.

10. A method for determining the position of an organ of a patient using at least two imaging devices, comprising the steps of:

making a first image of the organ with respect to a first coordinate system using a first imaging device;

placing the patient with respect to a second coordinate system;

determining a first position of a second imaging device with respect to the second coordinate system;

making a second image with said second imaging device;

matching the first image and the second image; and providing a third device having a third coordinate system and determining a first position of the third device with respect to the second image of the second imaging device, the third coordinate system of the third device positioned with respect to the second image of the second imaging device and with respect to the first image from the first imaging device.

* * * * *